(12) United States Patent
De Kraker et al.

(10) Patent No.: US 8,900,875 B2
(45) Date of Patent: Dec. 2, 2014

(54) DEVICE FOR EVALUATING A HEAT EXCHANGE FLUID

(75) Inventors: Abraham Robert De Kraker, Sugar Land, TX (US); Liliana Minevski, The Woodlands, TX (US); Tze Lee Phang, Katy, TX (US)

(73) Assignee: Shell Oil Company, Houston, TX (US)

( * ) Notice: Subject to any disclaimer, the term of this patent is extended or adjusted under 35 U.S.C. 154(b) by 749 days.

(21) Appl. No.: 13/140,136

(22) PCT Filed: Dec. 14, 2009

(86) PCT No.: PCT/US2009/067836
§ 371 (c)(1),
(2), (4) Date: Jul. 19, 2011

(87) PCT Pub. No.: WO2010/075025
PCT Pub. Date: Jul. 1, 2010

(65) Prior Publication Data
US 2011/0318843 A1 Dec. 29, 2011

Related U.S. Application Data

(60) Provisional application No. 61/122,837, filed on Dec. 16, 2008, provisional application No. 61/167,424, filed on Apr. 7, 2009.

(51) Int. Cl.
*G01N 21/29* (2006.01)
*G01N 31/22* (2006.01)
(Continued)

(52) U.S. Cl.
CPC .............. *G01N 31/221* (2013.01); *G01N 21/29* (2013.01); *G01N 21/80* (2013.01);
(Continued)

(58) Field of Classification Search
CPC .............. B01L 3/14; B01L 3/502; B01L 3/52; B01L 3/523; B01L 3/561; B01L 3/563; B01L 3/5635; B01L 99/00; B01L 2200/026; G01N 1/10; G01N 1/14; G01N 1/18; G01N 21/03; G01N 21/05; G01N 21/29; G01N 21/77; G01N 21/78; G01N 21/80; G01N 31/22; G01N 31/221; G01N 33/18; G01N 2001/1454; G01N 2001/4061; G01N 2021/03; G01N 2021/0325; G01N 2021/29; G01N 2021/77; G01N 2021/78; G01N 2033/18
USPC ......... 422/402, 408, 417, 419, 430, 501, 504, 422/514–515, 527, 544, 549–550, 559, 422/561–563; 436/129, 163–166, 177–178, 436/180
See application file for complete search history.

(56) References Cited

U.S. PATENT DOCUMENTS 3,493,503 A * 2/1970 Mass ............................. 210/778
3,692,490 A * 9/1972 Hall ............................. 422/542
(Continued)

*Primary Examiner* — Arlen Soderquist

(57) ABSTRACT

A method for assessing a corrosion inhibitor in a coolant, comprises providing a test kit comprising a first chamber containing an acid buffer and a solvent immiscible therein and a second chamber containing an indicator, the second chamber being in fluid communication with the first chamber and being configured such that retraction of the second chamber draws fluid into the first chamber and advancement forces fluid into the second chamber; drawing a coolant sample into the first chamber; contacting the coolant sample with the acid buffer and solvent in the first chamber and extracting the corrosion inhibitor into the solvent; allowing the solvent and buffer to separate in the first chamber; forcing a portion of the separated solvent into the second chamber; contacting the separated solvent with the indicator in the second chamber, and obtaining a visual indication of the presence of corrosion inhibitor in the coolant sample.

10 Claims, 7 Drawing Sheets

(51) Int. Cl.
| | | |
|---|---|---|
| *G01N 21/80* | (2006.01) | |
| *G01N 21/77* | (2006.01) | |
| *G01N 21/78* | (2006.01) | |
| *G01N 1/14* | (2006.01) | |
| *B01L 3/00* | (2006.01) | |
| *G01N 1/40* | (2006.01) | |
| *G01N 1/10* | (2006.01) | |

(52) U.S. Cl.
CPC ............... *G01N 21/77* (2013.01); *G01N 21/78* (2013.01); *G01N 1/14* (2013.01); *B01L 3/502* (2013.01); *B01L 3/523* (2013.01); *G01N 31/22* (2013.01); *G01N 2001/4061* (2013.01); *B01L 2200/026* (2013.01); *G01N 2001/1056* (2013.01)
USPC ........... 436/129; 422/402; 422/408; 422/417; 422/419; 422/430; 422/501; 422/504; 422/514; 422/527; 422/544; 422/549; 422/550; 422/559; 422/561; 422/562; 422/563; 436/163; 436/164; 436/165; 436/166; 436/177; 436/178; 436/180

(56) References Cited

U.S. PATENT DOCUMENTS

| | | | | |
|---|---|---|---|---|
| 3,715,189 | A * | 2/1973 | Nighohossian et al. ...... | 422/413 |
| 3,865,548 | A * | 2/1975 | Padawer ........................ | 436/165 |
| 3,910,764 | A * | 10/1975 | Tower .......................... | 422/430 |
| 3,955,423 | A * | 5/1976 | Ohringer ................... | 73/863.23 |
| 4,035,150 | A * | 7/1977 | Jaffe ............................... | 436/66 |
| 4,458,020 | A * | 7/1984 | Bohn et al. ................. | 435/287.2 |
| 4,585,623 | A * | 4/1986 | Chandler ...................... | 422/408 |
| 4,665,034 | A * | 5/1987 | Chandler ................... | 435/287.2 |
| 4,791,060 | A * | 12/1988 | Chandler ................... | 435/287.2 |
| 4,961,432 | A * | 10/1990 | Guirguis ....................... | 600/573 |
| 4,973,450 | A * | 11/1990 | Schluter ........................ | 422/535 |
| 5,312,593 | A * | 5/1994 | Rabenecker et al. ........... | 422/86 |
| 5,376,337 | A * | 12/1994 | Seymour ...................... | 422/419 |
| 5,658,531 | A * | 8/1997 | Cope et al. ................... | 422/410 |
| 5,800,782 | A * | 9/1998 | Hagstrom et al. .............. | 422/75 |
| 5,888,826 | A * | 3/1999 | Ostgaard et al. ................ | 436/69 |
| 5,952,233 | A | 9/1999 | Pellet et al. ....................... | 436/6 |
| 5,955,351 | A * | 9/1999 | Gerdes et al. .............. | 435/287.2 |
| 5,997,763 | A | 12/1999 | Pabon, Jr. et al. ............. | 252/79 |
| 6,153,425 | A * | 11/2000 | Kozwich et al. ............ | 435/287.2 |
| 6,475,438 | B2 | 11/2002 | Maes et al. | |
| 6,495,372 | B1 | 12/2002 | Maes et al. ..................... | 436/163 |
| 7,351,228 | B2 * | 4/2008 | Keane et al. .................. | 604/218 |
| 2004/0170533 | A1 * | 9/2004 | Chu .............................. | 422/100 |
| 2006/0222569 | A1 * | 10/2006 | Barten et al. .................. | 422/100 |
| 2007/0138434 | A1 | 6/2007 | Pellet et al. ..................... | 252/76 |
| 2008/0019873 | A1 | 1/2008 | Shah et al. .................... | 422/68.1 |

\* cited by examiner

DEVICE FOR EVALUATING A HEAT EXCHANGE FLUID

PRIORITY CLAIM

The present application claims priority from PCT/US2009/067836, filed 14 Dec. 2009, which claims priority from U.S. Provisional Applications 61/122,837, filed 16 Dec. 2008, and 61/167,424, filed 7 Apr. 2009, all of which are incorporated by reference.

FIELD OF THE INVENTION

The present invention relates generally to a device for evaluating the constituents of a heat exchange fluid having corrosion inhibitors therein. More particularly, the device provides a multi-chambered plunger that allows a multi-part chemical assessment to be carried out in with a minimum of operator inputs.

BACKGROUND OF THE INVENTION

The systems, apparatus, and methods described herein are particularly suited for determining the constituents of such heat exchange fluids as organic acid technology coolants. Referred to as "extended life coolants," these heat exchange fluids typically contain carboxylate salts of long-chain alkyl-based organic acids or of aromatic-based organic acids (hereinafter "acid-based corrosion inhibitors") as corrosion inhibitors. These corrosion inhibitors inhibit corrosion of the metallic surfaces that are contacted by the heat exchange fluid. The organic acid-based corrosion inhibitors are also formulated for longer or extended service lives as compared to inorganic acid-based corrosion inhibitors. The recommended service life for "extended life coolants" (ELC) (under normal driving conditions) is commonly about five years, whereas the recommended service life for conventional coolants may be about two years.

Corrosion inhibitors that are suitable for this use are known and include carboxylate salts of long chain alkyl monocarboxylic organic acids (such as 2-ethyl hexanoic acid, octanoic acid, etc.), of dicarboxylic acids (e.g., sebacic acid), or of aromatic organic acids (such as benzoic acids and p-toluic acids). An expanded description of the type of heat exchange fluid that is a subject of the present invention and its application are provided in U.S. Pat. Nos. 5,997,763 (commonly owned with the present application) and 6,475,438. Such heat exchange fluid types are widely used. It is further noted that the subject heat exchange fluids may be aqueous and/or glycol compositions and used for automotive, heavy duty, marine and other industrial applications.

The level of corrosion inhibitor(s) present in the coolant may diminish over time. For that reason, it may be desirable to test the coolant in order to determine its continued functionality. There is not currently available a reliable and convenient method or equipment for evaluating heat exchange fluids having corrosion inhibitors therein, so as to, for example, determine the sufficiency of the corrosion inhibitor content to provide ongoing corrosion protection. Analytical methods exist, but such methods typically require equipment, facilities and/or time that are not readily available or convenient to use in the field. Moreover, used heat exchange fluids typically include an array of components, including interferents. These interferents can alter the accuracy of conventional analytical techniques.

Thus it is desirable to provide a simple, easy-to-use device that can be used to determine the sufficiency of the corrosion inhibitor content, particularly in the field, where time and operator resources are relatively scarce.

SUMMARY OF THE INVENTION

In one embodiment of the present invention, a device is provided for evaluating the constituents of a heat exchange fluid having acid-based corrosion inhibitors therein. The invention provides a small, simple, fast, reliable, field-usable, and low-cost device for analyzing fresh, contaminated, and used extended life coolants and assessing their carboxylic acid-based inhibitor content. The device requires a minimum of operator steps and virtually no operator decision-making. Preferred embodiments include a multi-chambered device in which the flow between chambers is controlled by the configuration of the chambers themselves. More specifically, a preferred embodiment includes a device that can be operated merely by sequential retraction and advancement of a single plunger, without the need for manually controlled valves or other flow control methods.

In some embodiments, the invention comprises a method for assessing the presence of a corrosion inhibitor in a coolant comprising the steps of a) providing a test kit; b) retracting the second chamber so as to draw a sample of the coolant into the first chamber; c) contacting the coolant sample with the acid and the solvent in the first chamber so as to perform a liquid-liquid extraction of at least a portion of the corrosion inhibitor into the solvent; d) allowing at least a portion of the solvent to separate from the acid solution in the first chamber; e) advancing the second chamber so as to force at least a portion of the separated solvent into the second chamber; f) contacting the portion of separated solvent with the indicator solution in the second chamber so as to obtain a visual indication of the presence of corrosion inhibitor in the coolant sample.

The test kit may comprise a first chamber initially containing an acid buffer solution and a solvent, the solvent and the acid buffer being substantially immiscible and the solvent having a specific gravity that is less than that of said buffer solution, the first chamber including a first inlet and means for controlling fluid flow through the first inlet; and a second chamber initially containing an indicator solution and having a second inlet; wherein the second chamber is in fluid communication with the first chamber via the second inlet and the first and second chambers are configured such that retraction of the second chamber draws fluid into the first chamber through the first inlet and advancement of the second chamber forces fluid from the first chamber into the second chamber through the second inlet.

The device is such that the steps of the method can be carried out in less than one minute. The second chamber may be slidably received in the first chamber and the test kit may include a base that is capable of supporting the first chamber in an upright position and of sealing the first inlet. The indicator solution is preferably an acid-base indicator. The device is preferably free of manually controlled valves.

The present invention provides several advantages. For example, the result is independent of the color of the sample being tested, and the device is simpler than previously known devices.

BRIEF DESCRIPTION OF THE DRAWINGS

For a more detailed understanding of the preferred embodiments, reference is made to the accompanying Figures, wherein.

DETAILED DESCRIPTION OF THE INVENTION

The present invention provides a method, system, and apparatus for evaluating the constituents of a heat exchange fluid. The systems, apparatus, and methods described herein are particularly suited for determining the constituents of such heat exchange fluids that include organic acid technology coolants. Referred to as "extended life coolants," these heat exchange fluids typically contain carboxylate salts of long-chain alkyl-based organic acids or of aromatic-based organic acids (hereinafter "acid-based corrosion inhibitors") as corrosion inhibitors. These corrosion inhibitors inhibit corrosion of metallic surfaces with which the heat exchange fluid comes in contact. The organic acid-based corrosion inhibitors are also formulated for longer or extended service lives as compared to inorganic acid-based corrosion inhibitors. Suitable organic acid-based corrosion inhibitors include carboxylate salts of long chain alkyl monocarboxylic organic acids (such as 2-ethyl hexanoic acid, octanoic acid, etc.), of dicarboxylic acids (e.g., sebacic acid), or of aromatic organic acids (such as benzoic acids and p-toluic acids).

Figure 1:
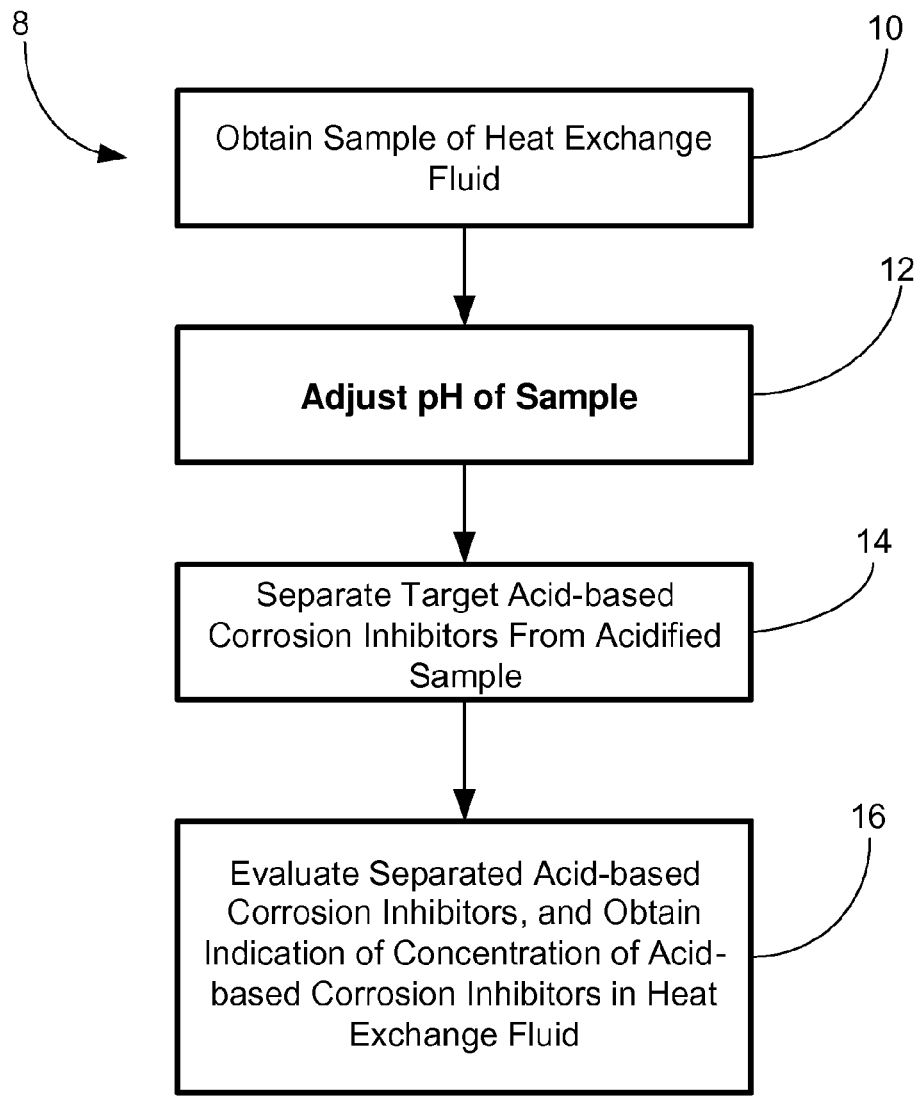
FIG. 1 is a simplified flowchart illustration of the steps carried out by preferred embodiments of the device of the present invention.
Figure 5:
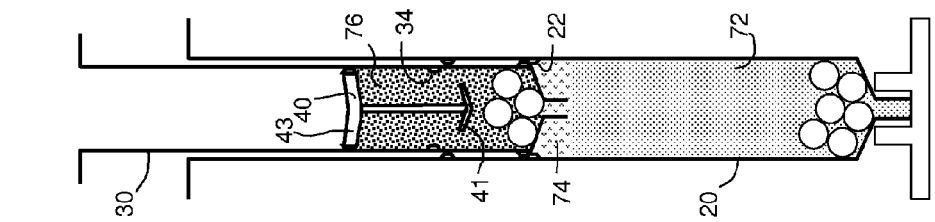
FIG. 5 is a schematic illustration of the device of FIG. 2 after the solvent has been contacted with an indicator

Preferred methods for analyzing the fluids are described in commonly-owned co-pending application Ser. No. 11/777, 066, which is incorporated herein by reference. As described therein and as illustrated in FIG. 1, the preferred analytical method includes the steps of:

- obtaining a sample of the heat exchange fluid (step 10), preferably in a predetermined amount;
- adjusting the pH of the sample so as to reduce the solubility of target acid-based corrosion inhibitors in the sample (step 12);
- separating the target acid-based corrosion inhibitors from the sample (step 14); and
- evaluating the separated residue containing the target acid-based corrosion inhibitors (step 16).

Step (12) results in the conversion of at least some (if not substantially all) of the salt form of the target acid-based corrosion inhibitors to its acid form. The acid forms of these corrosion inhibitors are much less soluble in water than the salt form and are, therefore, more susceptible to phase separation or liquid-liquid extraction. The objective of step (12) is to adjust the pH of the sample so as to at least render the target components susceptible to liquid-liquid extraction from the initial coolant solution, even if a complete physical phase separation has not occurred. In most applications, this requires the target corrosion inhibitor to be rendered at least partially insoluble.

According to the present invention, concurrently with its acidification, the sample is placed in contact with a solvent in which the carboxylic acid of the corrosion inhibitor is soluble. This brings about the separation shown as step (14), which is preferably carried out by liquid-liquid extraction. The carboxylic acid-containing solvent is then placed in contact with an indicator that changes color in the presence of an acid. Preferred embodiments of these steps are described in detail below.

Acid-based corrosion inhibitors that can be targeted and assessed using the methods of the present invention include but are not limited to organic acid-based corrosion inhibitors, and more particularly, carboxylate salts of long-chain organic acids such as alkyl monocarboxylic acids and dicarboxylic acids, and carboxylate salts of aromatic based monocarboxylic or dicarboxylic acids. In a typical application, the target corrosion inhibitors of interest may be composed of different groups of corrosion inhibiting compounds, such as groups of carboxylate salts of organic acids. These carboxylate salts may be present at different concentrations and their acidic forms may have different degrees of solubility in the solution. The target groups of compounds will be characterized by different pKa values. For each specific corrosion inhibitor acid, the exact pH at which phase separation initiates will depend on the total concentration of that specific inhibitor, the solubility limit of its protonated form in the solution, and the pKa of the inhibitor. If the pH of the sample is reduced to approximately the pKa value, depending on the concentration (i.e., its solubility limit) of one group of target corrosion inhibitors, that group of target corrosion inhibitors begins to phase separate from the solution and are more susceptible to extraction or separation from the solution. For each specific target corrosion inhibitor, as the total inhibitor concentration is lowered, phase separation is observed to occur at lower pH values.

Thus, in the present application, where the intent is to remove the corrosion inhibitors from a fluid sample so that their presence can be detected, the pH is reduced to well below the lowest pKa value of the group of targeted corrosion inhibitors. In the case where the total inhibitor concentration does not exceed the solubility limit of the acid form, phase separation of the inhibitor may not occur.

For all inhibitor organic acids, as the pH of the solution is preferably lowered by one, two, three or more pH units below the pKa value of the component of interest, the efficiency of separation is further improved because more of the carboxylate salt is driven by acid-base equilibrium into the carboxylic acid form. This lowering of the pH reduces solubility of the compound of interest in the aqueous solution and thus enables more efficient extraction of the compound, i.e. the carboxylic acid, into the solvent. The relative proportion of acid that is removed from the solution via the liquid extraction depends on the total concentration of the specific inhibitor and the solubility limit for the acid form of the specific inhibitor under consideration.

In preferred embodiments, the portion of the sample that is dissolved in the solvent contains the target organic acid-based corrosion inhibitors and excludes corrosive short-chain organic acids and other analytical interferents that would otherwise affect some measurement methods (e.g., titration). The excluded interferents preferably include organic acids that are glycol oxidation products (e.g., glycolic acid or formic acid, and inorganic acid components such as silicates, borates, phosphates, nitrites and nitrates).

Referring again to FIG. 1, following the separation step, the solvent containing the target acid-based corrosion inhibitors is measured or otherwise evaluated, in step (16), using one of a number of commonly known analytical methods. As will be described below, the sufficiency of the amount of corrosion inhibitors retained in the heat exchange fluid may be evaluated qualitatively or quantitatively. Suitable measurement methods may involve a titration process and/or chemical reactions. For example, the acidity of the solvent may be analyzed using an acid-base color indicator. In this embodiment, the indication of a color change can be used to indicate that the concentration of acid-based corrosion inhibitors in the sample is equal to, above, or below a predetermined level.

Referring now to FIGS. 2-5, a preferred system and/or apparatus for carrying out the method described above is a portable, field-ready kit that includes all of the components and prepared solutions necessary for performing the evaluation described above. Using a single field kit, a qualitative analysis can be performed to determine whether the concentration of target corrosion inhibitors in the heat exchange fluid is below or above a predetermined level.

Figure 2:
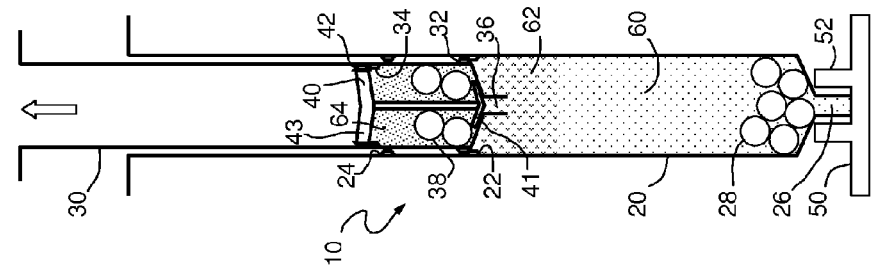
FIG. 2 is a schematic illustration of one embodiment of a device constructed in accordance with the present invention, in an initial state.

Referring first to FIG. 2, an exemplary device 10 for evaluating the concentration of acid-based corrosion inhibitors contained in a heat exchange fluid includes a first chamber 20, a second chamber 30, a plunger 40, and a base 50.

First chamber 20 preferably includes a hollow cylindrical body having an inlet 26 at one end and an open second end. The inner wall of chamber 20 includes a first stop member 22 positioned at a first distance from inlet 26 and a second stop member 24 positioned at a second, greater distance from inlet 26. Stop members 22, 24 may be annular ridges on the inside wall of chamber 20 or any other similar device. A plurality of mixing elements 28 are optionally contained in chamber 20. Mixing elements 28 may be glass balls or any other small solid objects that will not interact with the chemical components of the present invention.

Second chamber 30 is slidably received in chamber 20. Like chamber 20, chamber 30 preferably includes a hollow cylindrical body having an inlet 36 at one end and an open second end. The outside diameter of second chamber 30 is incrementally smaller than the inside diameter of chamber 20, so that a sealing engagement can be formed between the inside surface of chamber 20 and the outside of chamber 30. The seal may be formed using stop members 22, 24, or using other seal members (not shown). Chamber 30 includes a first stop member 32 at one end, preferably positioned adjacent to inlet 36, and an optional second stop member 34 positioned at some distance from first stop member 32. First stop member 32 is disposed on the outside surface of chamber 30 and may form part of the sealing engagement with the inside wall of chamber 20. Second stop member 34 is disposed on the inside surface of chamber 30. A plurality of mixing elements 38 are optionally contained in chamber 30. Mixing elements 38 may be glass balls or any other small solid objects that will not interact with the chemical components of the present invention.

Plunger 40 is slidably received in chamber 30. Plunger 40 preferably comprises a body having a first end 41 and a second end 43. Second end 43 is provided with seal/stop member 42, which forms a sliding sealing engagement with the inside surface of chamber 30. Plunger 40 is preferably sized so that first end 41 closes inlet 36 before or when stop member 42 engages stop member 34.

Before use, chamber 30 is advanced into chamber 20 such that stop member 32 engages stop member 22 and plunger 40 is advanced into chamber 30 such that stop member 42 engages stop member 34 and end 41 closes inlet 36 so that fluid flow between chamber 20 and chamber 30 is prevented. It will be understood that other devices for closing inlet 36 can be used, including but not limited to flapper valves, check valves, and the like. In some embodiments, fluid flow between first chamber 20 and second chamber 30 is prevented by providing an air gap above the liquid surface in chamber 20, so that an air bubble occupies inlet 36 during the mixing process. Thus, in some embodiments, inlet 36 has a relatively small inside diameter.

First chamber 20 is preferably preloaded with an acid solution, shown at 60, and a solvent, shown at 62. Acid solution 60 may be a buffer solution. Acid solution 60 and solvent 62 are preferably immiscible and are preferably selected such that the specific gravity of the solvent is less than that of the buffer solution. By way of example only, the acid solution may comprise 0.1N $Na_2HPO_4$ in DI water, plus ~2% concentrated $H_3PO_4$ to obtain pH 2.2 and the solvent may comprise dibutyl ether, isopropyl ether, methyl isobutyl ketone, or the like. Second chamber 30 is preferably preloaded with an indicator solution, shown at 64. Indicator 64 may comprise, for example, 0.1N NaOH in DI water/ethanol 1/3, plus 0.02 wt % bromothymol blue pH indicator. Solvent 62 and indicator 64 may or may not be miscible, as desired.

Acid buffers suitable for use with the invention (as the acidifying solution) are generally known. Typically, acid buffers are a mixture of an acid and its salt. Examples of suitable acid buffer systems include HCl/KCl systems (pH=1-2), sodium dihydrogen phosphate/phosphoric acid systems (pH=2-4), potassium tetraoxalate systems (pH=1-2), acetic acid/sodium acetate (pH=3-6), HCl/citric acid systems (pH=1-5). A suitable acid buffer system will have a reactive acid capacity to react with the basic buffers of the ELC coolant systems and neutralize these basic buffers while controlling the pH of the final mixture. The corrosive nature of the acid reagent is thus minimized.

In general, any readily available acid capable of reducing the pH of the sample fluid may be used as the acidifying solution instead of an acid buffer. Acids such as hydrochloric acid, sulfuric acid, nitric acid, or phosphoric acid (i.e. 0.1 molar to 1 molar in concentration) may be used.

Referring again to FIG. 2, base 50 is preferably sufficiently stable to support device 10 in an upright position. To that end, base 50 may include a receptacle 52 sized to receive the inlet 26 of chamber 20. In some embodiments, the inside of receptacle 52 and the outside of inlet 26 may be provided with mating threads, luer taper fittings, snap fittings, or other similar sealing device (not shown) therebetween so that base 50 may also function as a cap or closure for chamber 20. It will be understood that a valve or similar device can also be included to control the flow of fluid through inlet 26 if desired. In such an embodiment, it is not necessary for base 50 to function as a cap.

Because the present device provides a visual output and depends in part on visual verification of the process steps, it is preferred that the components of the device, and in particular chambers 20 and 30, be constructed of a clear or at least partially transparent material.

Operation

Figure 3:
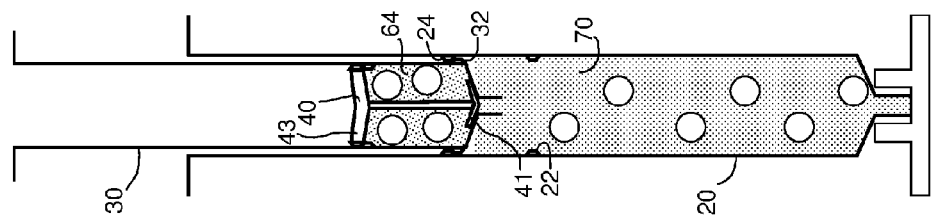
FIG. 3 is a schematic illustration of the device of FIG. 2 after a sample has been collected.

When it is desired to use device 10 to assess a sample of fluid, base 50 is removed from chamber 20 and a sample of coolant is drawn into chamber 20 by retracting chamber 30 until stop member 32 engages stop member 24, as shown in FIG. 3. By way of example only, the distance between stop member 22 and stop member 24 may be such that the volume of sample obtained in this manner is about 1 ml. If necessary, cap 50 is then replaced and the device is preferably shaken so as to cause thorough mixing of the sample, acid solution 60 and solvent 62 in chamber 20. If present, mixing elements 28 enhance the contact between the solutions. A mixture, shown at 70 in FIG. 3, is temporarily formed in chamber 20 during this process. Because the pH of the acid solution is low, salts of the corrosion inhibiting compounds are converted to their carboxylic acid forms, which have reduced solubility in the aqueous phase. At the same time, the carboxylic acids are soluble in the solvent, with the result that some of the corrosion-inhibiting compounds migrate into the solvent.

Figure 4:
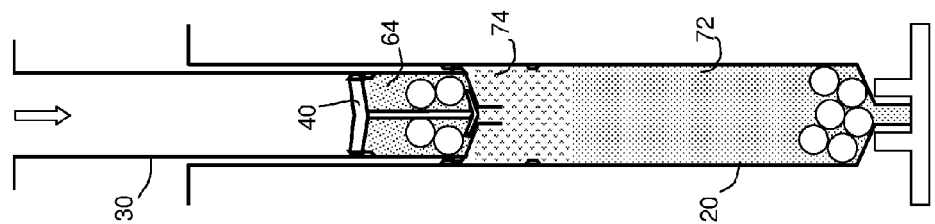
FIG. 4 is a schematic illustration of the device of FIG. 2 after phase separation has occurred.

If the cap is not already in place, chamber 20 is then placed in base 50, and the mixture is allowed to rest. As shown in FIG. 4, during the rest period, the carboxylic acid-containing solvent solution 74 separates from the mixture 72 containing the sample and the acid solution. In most instances, separation is sufficiently complete in 30 to 120 seconds. It has been found that a visual determination that separation is complete is sufficiently precise to allow for meaningful assessment of the coolant sample.

Once the solvent has separated from the aqueous phase in chamber 20, chamber 30 is advanced into chamber 20 until stop member 32 again engages stop member 22. With cap 50 in place or inlet 26 closed by other means, movement of chamber 30 within chamber 20 forces a portion of the solvent phase, which is uppermost in chamber 20, to enter chamber 30, which in turn causes plunger 40 to retract along chamber 30 so as to accommodate the additional fluid volume in chamber 30. The amount of solvent solution 74 that enters chamber 30 is preferably less than the total amount of solvent, so as to ensure that the mixture in chamber 30 is not contaminated with the sample/acid solution 72.

Once inside plunger 40, solvent solution 74 mixes with the indicator solution there, forming a sample indicator solution 76. The presence of sufficient organic acid in the solvent phase will neutralize the base, causing the sample indicator solution to become acidic and change color. If the amounts, compositions, and concentrations of the solutions provided with the device are selected appropriately, the presence or absence of a color change in the indicator solution can be used as an indicator of the presence or degree of degradation of the corrosion inhibitor.

For example, a color change may indicate that the concentration of acid inhibitors in the sample is in excess or equal to a predetermined threshold concentration. This predetermined threshold amount preferably corresponds to the desired threshold or minimum concentration of acid inhibitors in the heat exchange fluid in use. It should be noted that any appropriate indicator may be used for indicating or detecting the threshold concentration of acid inhibitors.

The preferred method described above is particularly advantageous over prior art methods of testing extended life coolant/heat exchange fluids to determine the content of acid-based corrosion inhibitors. In the above-described method, the long-chain alkyl and the aromatic organic acids, such as the carboxylic acid-based corrosion inhibitors, are excluded from the rest of the sample, and particularly from corrosive short-chain organic acids and other acidic interferents. In this way, after separation, measurement of organic acids will only detect the targeted organic acids (i.e., the target corrosion inhibitors). The measurement will not be affected or interfered by inclusion of short-chain organic acids and other acidic interferents, including inorganic acids.

In addition, the present invention provides an indication of coolant composition that is not dependent on the color or appearance of the original coolant sample. It has been found that the dyes typically used in coolant compositions are not soluble in the solvent phase 62, and thus do not interfere with the color of the indicator 64.

It is not uncommon for consumers to mix extended life coolants with other heat exchange fluids. A common mixture may include short-chain organic acids, which are formed unintentionally by oxidation of glycol, and inorganic corrosion inhibitors along with long-chain organic acid-based corrosion inhibitors. Hybrid extended-life coolants also contain a mixture of inorganic and long-chain organic acid-based corrosion inhibitors. In one preferred method, only the corrosion inhibitors that render the heat exchange fluid to be "extended life" are detected. Accordingly, in a quantitative measurement, the amount of "extended life" additives or coolant required to replenish the mixture and preserve its extended life can be determined.

The method, system, and apparatus described above provide a reliable, field ready and convenient method for analyzing the heat exchange fluids. The system and apparatus described above are particularly useful for original equipment manufacturers (OEMs), fleet owners, and automotive shops (e.g., truck stops or fast lube facilities). One benefit of the described method, systems, and apparatus, is that it provides a quick, efficient, and accurate quantitative field method for determining the residual content of target acid-based corrosion inhibitors in either fresh, contaminated, or used extended life heat exchange fluids. The method may be used to determine the concentration of acid-based corrosion inhibitors in order to determine the heat exchange fluid's utility for continued use or, alternatively, to determine how much of any fresh corrosion inhibitors may be added to maintain the heat exchange fluid's utility.

Because the present device requires only retraction and depression of a single plunger and no control or decision steps, it is extremely simple to use. Accordingly, it is contemplated that the invention will be particularly beneficial to OEM's, fleet owners, the automobile service industry, and every day automobile owners. The mechanic, maintenance personnel, or car owner can accurately determine the concentration or level of acid-based inhibitors present in heat exchange fluid samples or whether the concentration or level in the heat exchange fluid is above or equal to a predetermined minimum threshold. With this information, the same personnel can determine the sufficiency of the heat exchange fluid for continued use and/or determine how much, if any, of fresh coolant must be added to maintain the utility of the coolant.

In an alternative embodiment of the invention, the separation can be carried out using a multi-chambered device as illustrated in FIGS. 6-10. This embodiment is also described in U.S. application Ser. No. 61/122,837, which is incorporated herein by reference in its entirety.

Figure 6:
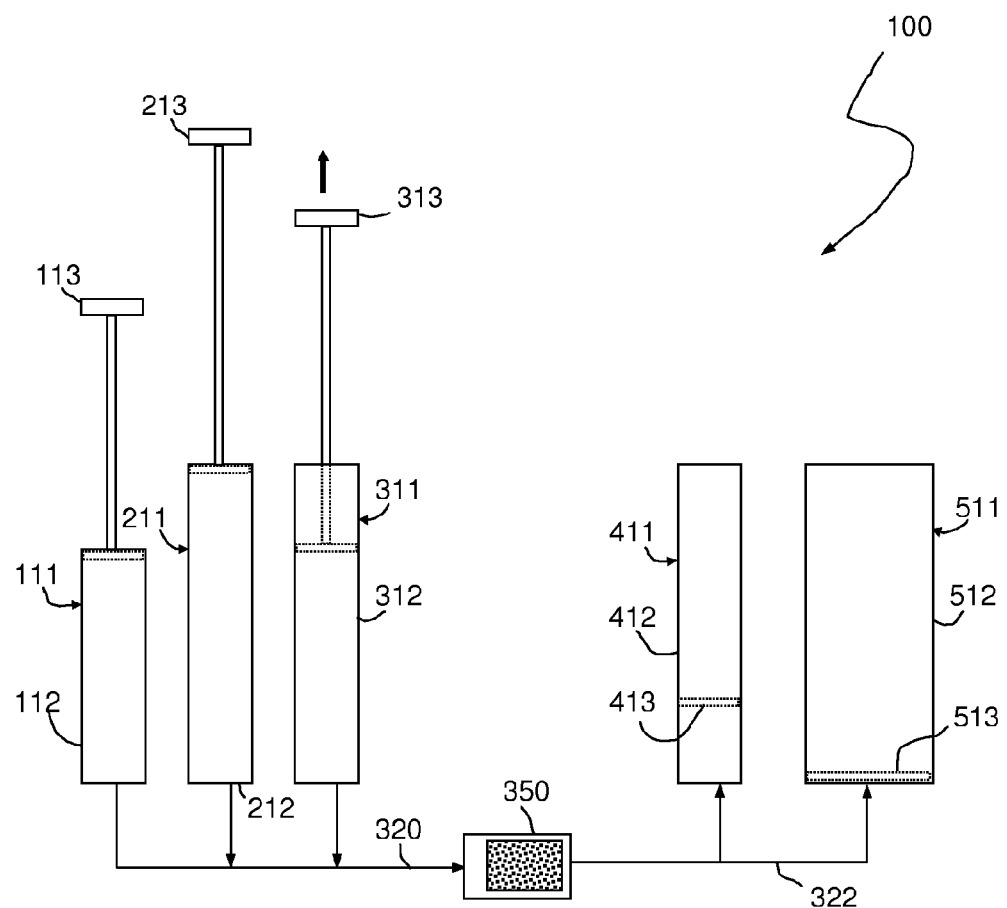
FIG. 6 is a schematic illustration of a device constructed in accordance with another embodiment the present invention, in an initial state.

A preferred system and/or apparatus for carrying out the method described above is a portable, field-ready kit, as shown schematically in FIG. 6. Such a "field kit" may include all the components and prepared solutions necessary for performing the general evaluation method described above. Using a single field kit, a qualitative analysis can be performed to determine whether the concentration of target corrosion inhibitors in the heat exchange fluid is below or above a predetermined level.

Referring now to FIG. 6, an exemplary system 100 for evaluating the concentration of acid-based corrosion inhibitors contained in a heat exchange fluid includes five variable-volume chambers 111, 211, 311, 411, 511. Chambers 111-311 are dispensing chambers and preferably each comprise a barrel 112, 212, 312 and a corresponding plunger/piston 113, 213, 313, whereas receiving chambers 411 and 511 each preferably comprise a barrel 412, 512 and a handleless piston 413, 513 (shown in phantom). Chambers 111-511 may comprise or resemble conventional syringes or any other suitable mechanism for controllably collecting, holding and releasing fluids. For example, it will be understood that dispensing chambers 111-311 may be constructed in any manner that allows them to be easily manually operated. Thus, by way of example only, instead of plungers the volume of each chamber may be reduced by means of a thumbwheel or the chambers themselves may comprise compressible containers.

The volume of chamber 511 is preferably equal to the sum of the volumes of chambers 211 and 311. In preferred embodiments, the area of piston 513 is greater than the area of piston 413, and more particularly at least twice as great as the area of piston 413. In some embodiments, the volumes of chambers 211 and 311 are equal. The volume of chamber 411 is preferably equal to the volume of chamber 111 plus the volume of a predetermined amount of indicator solution.

Dispensing chambers 111, 211, 311 are preferably connected in parallel to an extraction device 350, which may be a membrane, sorbent, or the like, as described above. Likewise, receiving chambers 411, 511 are preferably connected in parallel downstream of extraction device 350. One or more of the chambers and in particular chamber 311 may be releasably connected to the system, so as to allow chamber 311 to be used for collection of the sample to be assessed.

As illustrated in FIG. 6, before usage of the device, chamber 311 preferably contains a predetermined volume of an acidifying solution or buffer that will reduce the pH of the sample fluid below a predetermined level. The volume of acidifying solution or buffer is preferably smaller than the total volume of chamber 311 so that there is room in chamber 311 to also accommodate a sample volume in addition to the acidifying solution or buffer. Chamber 211 contains a wash solution as described in detail below. Chamber 111 contains a solvent, again as described in detail below.

Operation

Figure 7:
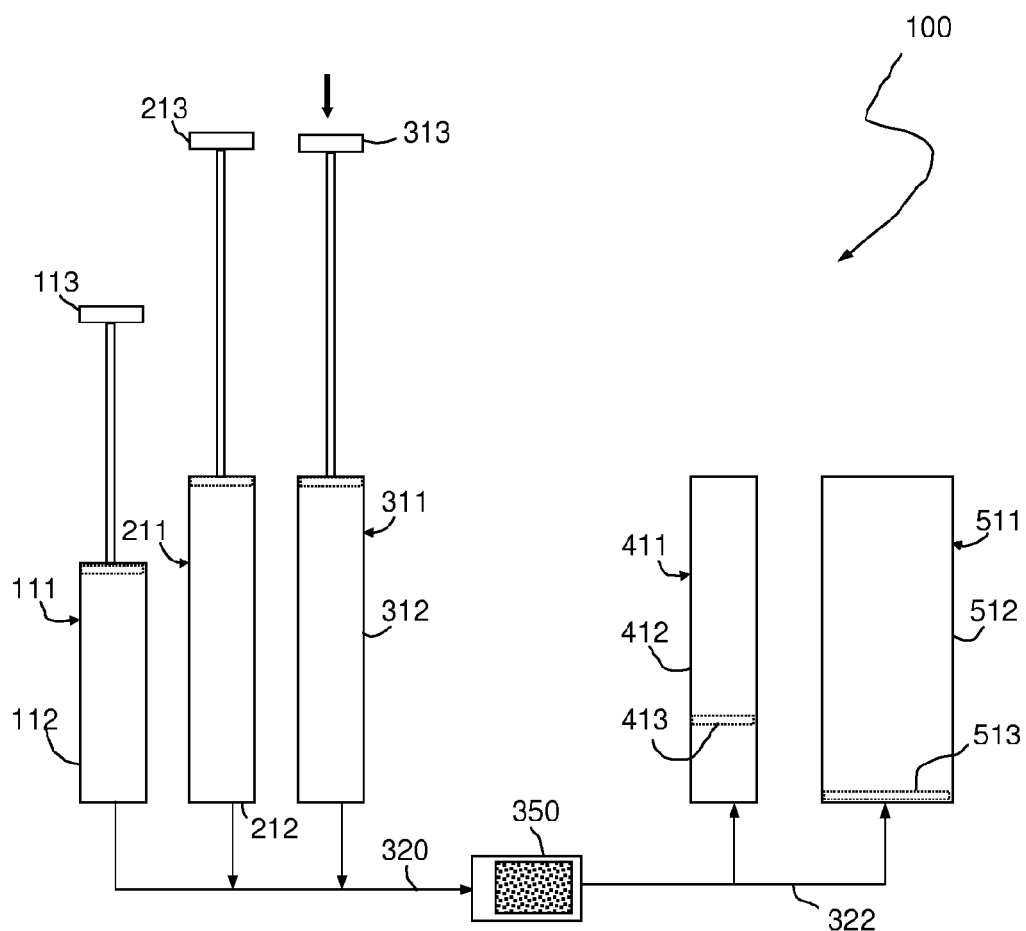
FIG. 7 is a schematic illustration of one the device of FIG. 6 after a sample has been collected.

When it is desired to assess a sample of coolant, chamber 311 may be removed from the kit and used to collect the desired sample. If chamber 311 is preloaded with a volume of acid or buffer, the sample may be drawn into chamber 311 and allowed to mix with the preloaded liquid. In preferred embodiments, chamber 311 is sized such that its total volume is equal to sum of the initial volume of acidifying solution and the desired sample size, so the chamber 311 is full after the sample has been collected, as shown in FIG. 7.

In the case where the sample is being assessed for the presence of acid-based corrosion inhibitors, the pH of the resultant acidified sample in chamber 311 is preferably below about 6 and, more preferably, within the range of about 2 to about 4. In this way, the target corrosion inhibitor organic acids in the sample fluid are rendered insoluble, or substantially insoluble, in the acidified sample.

Acid buffers suitable for use with the invention (as the acidifying solution) are generally known. Typically, acid buffers are a mixture of an acid and its salt. Examples of suitable acid buffer systems include HCl/KCl systems (pH=1-2), sodium dihydrogen phosphate/phosphoric acid systems (pH=2-4), potassium tetraoxalate systems (pH=1-2), acetic acid/sodium acetate (pH=3-6), HCl/citric acid systems (pH=1-5). A suitable acid buffer system will have a reactive acid capacity to react with the basic buffers of the ELC coolant systems and neutralize these basic buffers while controlling the pH of the final mixture. The corrosive nature of the acid reagent is thus minimized.

In general, any readily available acid capable of reducing the pH of the sample fluid in the preloading step as desired may be used as the acidifying solution instead of an acid buffer. Acids such as hydrochloric acid, sulfuric acid, nitric acid, or phosphoric acid (i.e. 0.1 molar to 1 molar in concentration) may be used. These concentrated acids will also neutralize the basic ELC coolant media and reduce the pH for the intended purpose. The use of these acids will require, however, that operating procedures are specifically implemented, and operating equipment designed, for the handling of corrosive materials.

Figure 8:
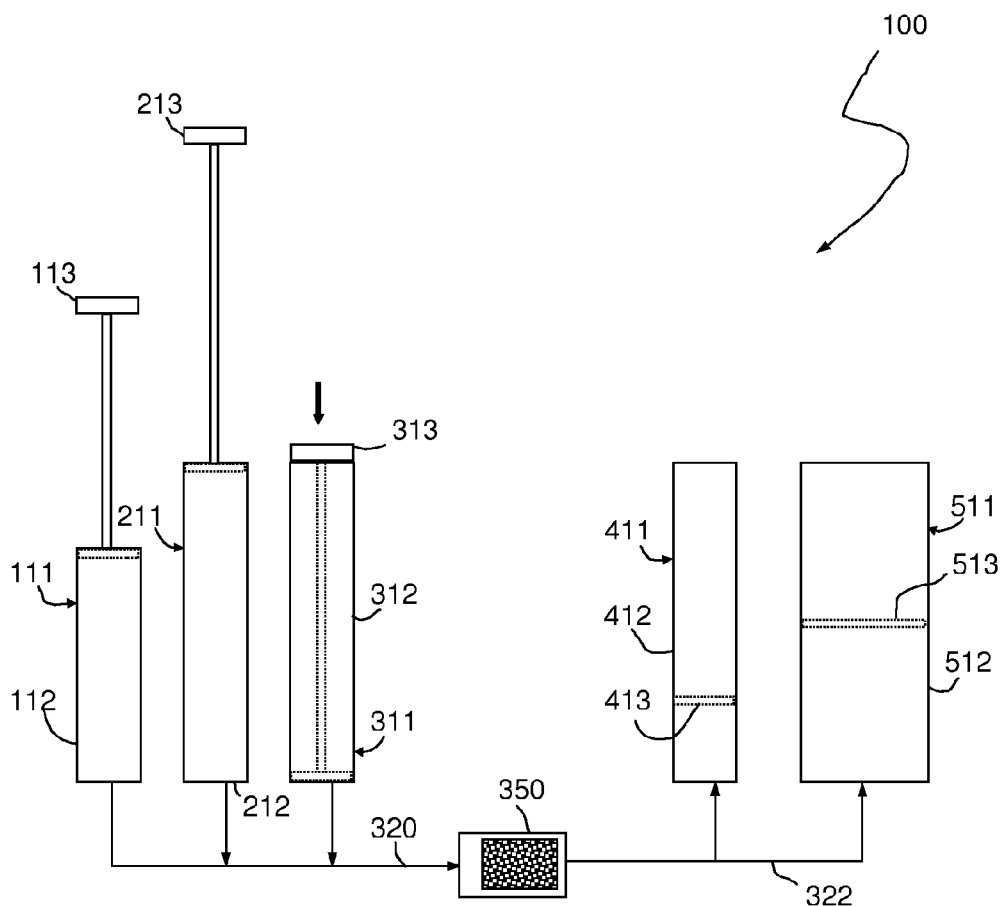
FIG. 8 is a schematic illustration of one the device of FIG. 6 after a first dispensing chamber has been emptied.

Chamber 311 is designed to enable coolant and acidifying solution to be mixed just prior to, or during, manual injection of the acidified sample into the extraction device. In preferred embodiments, the resulting mixture is injected into the extraction device by depressing plunger 313, as illustrated in FIG. 8. Because chambers 111 and 211 are already full at this point, no fluid flows into them. Instead, the contents of chamber 311 flow into extraction device 350. If the extraction device is an SPE cartridge, the pH-adjusted sample is preferably injected into the extraction device 350 at a rate that is sufficiently slow to allow adsorption of target organic acids from the acidified sample onto the SPE cartridge. In this process, most of the heat exchange fluid and water-soluble components of the fluid (including corrosive short-chain organic acids and inorganic acids) pass through the SPE cartridge.

Fluid flowing out of extraction device 350 flows into line 322. Because there is preferably no valving in line 322, fluid pressure at the entrances to receiving chambers 411 and 511 will be substantially the same. However, because the area of piston 513 is greater than the area of piston 413, the pressure of fluid flowing out of extraction device 350 will apply a greater force to piston 513 than to piston 413, causing it to move sooner and faster than piston 413. In addition, the interface between piston 513 and the inside wall of chamber 511 may be designed to have lower coefficients of static and/or dynamic friction than the interface between the piston 413 and the inside wall of chamber 411, so that piston 513 is still more likely to move farther than piston 413. These differences between chambers 411 and 511 cause the majority of the fluid to enter chamber 511, as illustrated in FIG. 8.

Referring again to FIG. 6, chamber 211 contains a predetermined volume of wash solution, which may comprise water that has been acidified to a desired pH. For example, the pH of the water may be in the range of about 3 to 4. The wash solution is preferably selected to have a pH that is not so low as to cause error in a subsequent analytical procedure but not so high as to cause the corrosion inhibitor organic acids to re-dissolve. The wash solution may be prepared by diluting a strong acid, such as hydrochloric acid, to a low concentration in distilled water, or by any other suitable technique, such as are known in the art.

Figure 9:
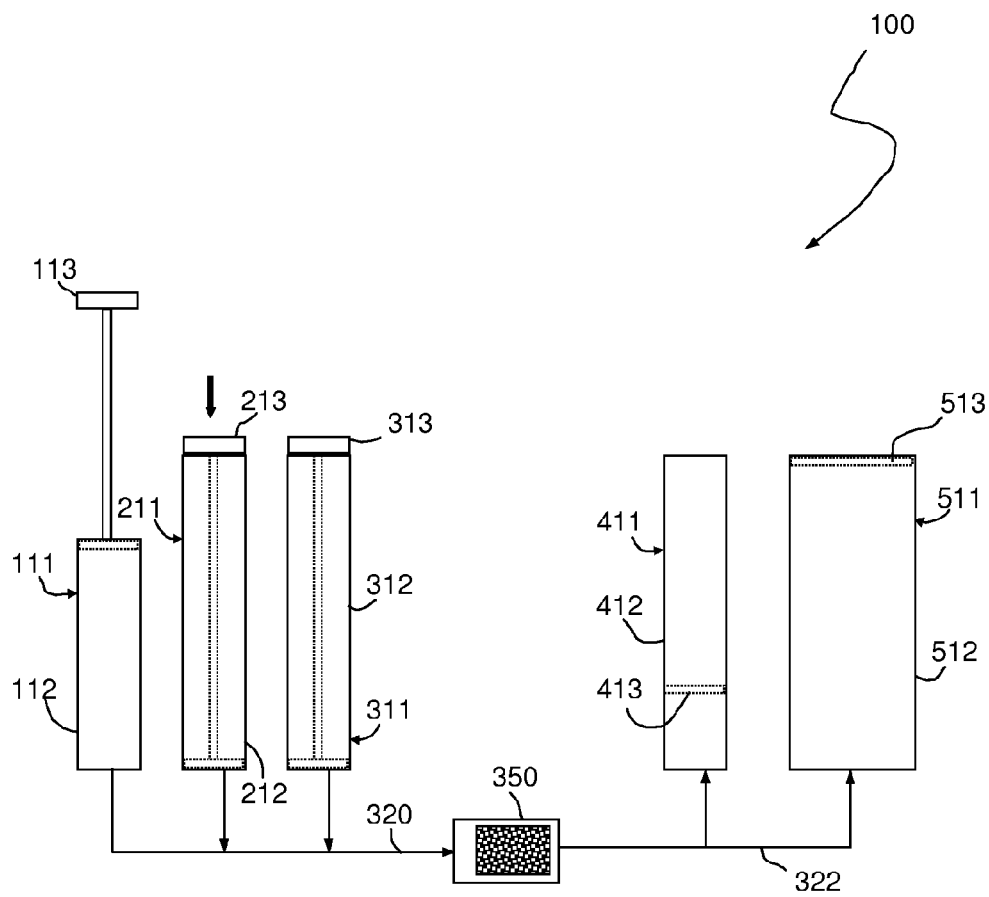
FIG. 9 is a schematic illustration of one the device of FIG. 6 after a second dispensing chamber has been emptied.

The wash solution is used to rinse the SPE cartridge or other extraction device and to wash away water-soluble acids, salts, and buffer components and separate them from the corrosion inhibitor organic acids, which remain in the extraction device. Thus, when plunger 213 is depressed fully as shown in FIG. 9, the fluid from chamber 211 flows through extraction device 350. Again, the fluid flows into line 322 and applies equal pressure at the entrances to chambers 411 and 511. Again, the majority of the fluid enters chamber 511, as shown in FIG. 9.

Finally, plunger 113 may be depressed so as to cause dispensing chamber 111 to inject a solvent into line 320. Any organic solvents or organic solvent mixtures that can desorb and dissolve the organic acid ELC compound from extraction device 350 may be used as the solvent. Suitable organic solvents include alcohols such as methanol, ethanol, and isopropanol. Other polar organic solvents such as acetone and tetrahydrofuran are also suitable provided these are applied in an appropriate manner.

Figure 10:
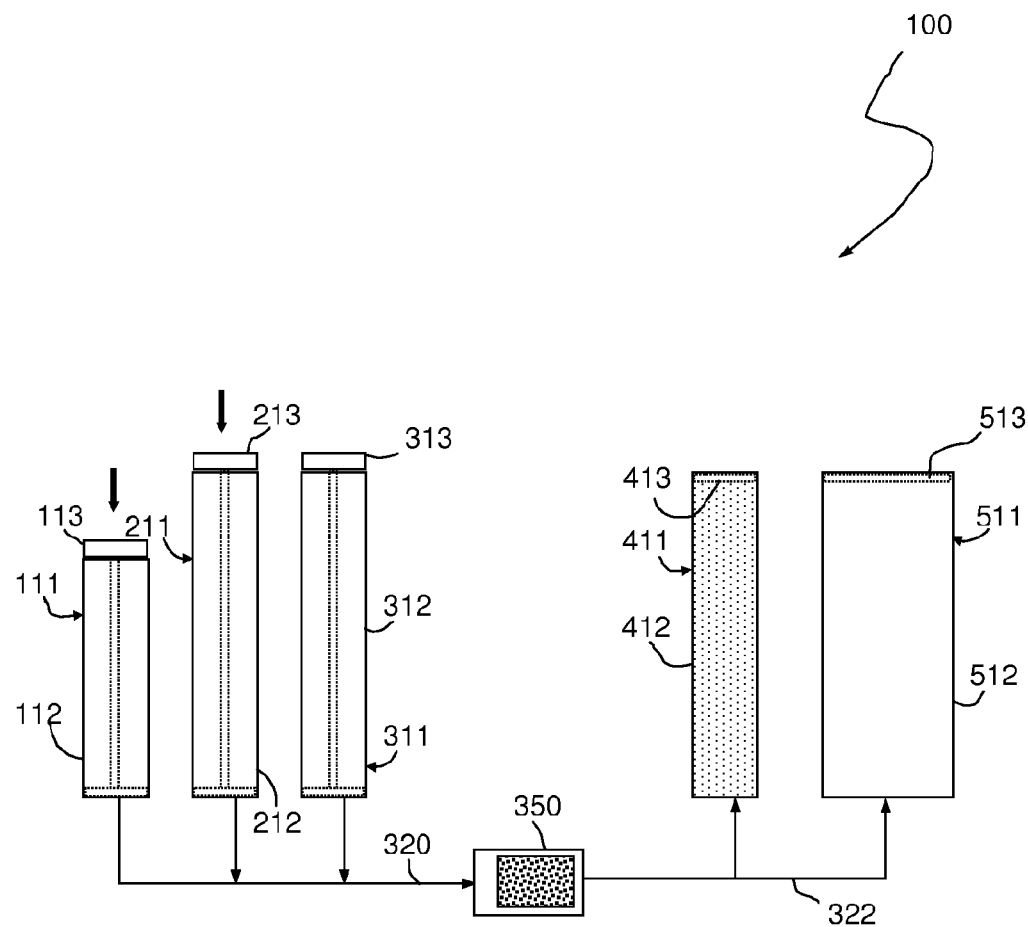
FIG. 10 is a schematic illustration of one the device of FIG. 6 after a third dispensing chamber has been emptied.

The organic solvent elutes the target organic acids (i.e., corrosion inhibitors of interest) from extraction device 350. However, at this point, chamber 511 is completely or nearly completely filled with the contents of chambers 311, 211, and the sample fluid. Thus, the eluent comprising solvent and dissolved/desorbed compounds is forced to flow into chamber 411, as shown in FIG. 10. As mentioned above, chamber 411 contains a predetermined amount of an indicator, which mixes with the solvent as plunger 113 is depressed and the solvent flows through extraction device 350 and into chamber 411.

In one embodiment, chamber 411 holds a prepared solution of a base (e.g., 0.1 molar sodium hydroxide in water) (a "standardized base solution") and a suitable acid-base color indicator, such as are known. The entire device 100 can be shaken or inverted several times to mix the contents of chamber 411. In some embodiments, chamber 411 may be removed from the test kit, capped, and then shaken to mix the organic solvent solution and the indicator/base solution. This ensures a quantitative reaction between the eluted organic acids in organic solvent and the base.

A color change indicates that the concentration of acid inhibitors in the eluent is in excess or equal to a predetermined threshold concentration. This predetermined threshold amount preferably corresponds to the desired threshold or minimum concentration of acid inhibitors in the heat exchange fluid in use. It should be noted that any appropriate indicator may be used for indicating or detecting the threshold concentration of acid inhibitors.

Because the present device requires only sequential emptying of the dispensing chambers 111-311, without any additional control steps, the present method is relatively simple. Accordingly, it is contemplated that the invention will be particularly beneficial to OEM's, fleet owners, the automobile service industry, and every day automobile owners. The mechanic, maintenance personnel, or car owner can accurately determine the concentration or level of acid-based inhibitors present in heat exchange fluid samples or whether the concentration or level in the heat exchange fluid is above or equal to a predetermined minimum threshold. With this information, the same personnel can determine the sufficiency of the heat exchange fluid for continued use and/or determine how much, if any, of fresh coolant must be added to maintain the utility of the coolant.

It should be noted that the methods, systems, and apparatus described herein may be applicable to fluids other than the heat exchange fluids specifically described herein. Likewise, the evaluating methods described herein may be performed manually or, by using an automated system and/or apparatus.

The foregoing description is presented for purposes of illustration and is not intended to limit the invention (as defined by the following claims) to the form described. Although several embodiments of the testing method, system and apparatus have been shown or described, alternative embodiments will be apparent to those skilled in the chemical, instrumentation, and other relevant art. For example, the various evaluation methods may be employed to evaluate other heat exchange fluid compositions not described herein. Moreover, the evaluation methods may be employed in conjunction with use of other testing components or arrangements. The embodiments described are further intended to explain the best mode of practicing the invention and to enable others skilled in the art to utilize the invention in such, or other, embodiments.

The invention claimed is:

1. A method for assessing the presence of a corrosion inhibitor in a coolant sample, comprising the steps of:
  a) providing a test kit comprising:
    a first chamber comprising a first inlet, wherein the first chamber initially contains an acid solution and a solvent, the solvent and the acid solution being substantially immiscible and the solvent having a specific gravity that is less than that of the acid solution;
    a second chamber comprising a second inlet, wherein the second chamber initially contains an indicator solution; and
    a based configured to selectively close the first inlet, wherein the second chamber is configured to be slidably received in the first chamber and in fluid communication with the first chamber via the second inlet, and the first and second chambers are configured such that, when the first inlet is not closed, retraction of the second chamber draws fluid into the first chamber through the first inlet and, when the first inlet is closed, advancement of the second chamber forces fluid from the first chamber into the second chamber through the second inlet;
  b) with the first inlet not closed, retracting the second chamber from the first chamber so as to draw the coolant sample into the first chamber via the first inlet;
  c) closing the first inlet with the base;
  d) allowing contact between the coolant sample, the acid solution and the solvent in the first chamber so as to perform a liquid-liquid extraction of at least a portion of the corrosion inhibitor into the solvent;
  e) allowing at least a portion of the solvent to separate from the acid solution in the first chamber;
  f) with the first inlet closed, advancing the second chamber so as to force at least a portion of the separated solvent from the first chamber into the second chamber;
  g) allowing contact between the portion of the separated solvent and the indicator solution in the second chamber so as to obtain a visual indication of the presence of the corrosion inhibitor.

2. The method of claim 1 wherein steps b)-g) are carried out in less than one minute.

3. The method of claim 1 wherein the base is configured to support the first chamber in an upright position.

4. The method of claim 1 wherein the indicator solution is an acid-base indicator.

5. The method of claim 1 wherein the base is a cap.

6. A test kit for assessing a fluid, comprising:
  a first chamber comprising a first inlet, wherein the first chamber contains an acid solution and a solvent, the solvent and the acid solution being substantially immiscible and the solvent having a specific gravity that is less than that of the acid solution;
  a second chamber comprising a second inlet, wherein the second chamber contains an indicator solution; and
  a base configured to selectively close the first inlet,
  wherein the second chamber is configured to be slidably received in the first chamber and in fluid communication with the first chamber via the second inlet, and the first and second chambers are configured such that, when the first inlet is not closed, retraction of the second chamber draws fluid into the first chamber through the first inlet and, when the first inlet is closed, advancement of the second chamber forces fluid from the first chamber into the second chamber through the second inlet.

7. The test kit of claim 6 wherein the test kit is free of manually controlled valves.

8. The test kit of claim 6, wherein the base is configured to support the first chamber in an upright position.

9. The kit of claim 6 wherein the indicator solution is an acid-base indicator.

10. The test kit of claim 6 wherein the base is a cap.

* * * * *